United States Patent [19]

Kohno et al.

[11] 4,334,431
[45] Jun. 15, 1982

[54] ULTRASONIC MEASURING INSTRUMENT

[75] Inventors: Masaru Kohno; Yukia Nakagawa; Takeo Kada; Gunzi Okawara, all of Kawasaki, Japan

[73] Assignee: Fuji Electric Company, Ltd., Tokyo, Japan

[21] Appl. No.: 64,820

[22] Filed: Aug. 8, 1979

[30] Foreign Application Priority Data

Aug. 9, 1978 [JP] Japan .................................. 53/96953

[51] Int. Cl.³ ........................ G01F 1/66; G01N 29/02
[52] U.S. Cl. .................................... 73/597; 73/861.27
[58] Field of Search ................ 73/597, 861.27, 861.28, 73/861.31

[56] References Cited

U.S. PATENT DOCUMENTS

| | | | |
|---|---|---|---|
| 3,697,936 | 10/1972 | Zacharias, Jr. et al. | 73/597 X |
| 3,818,757 | 6/1974 | Brown | 73/861.28 |
| 4,028,938 | 6/1977 | Eck | 73/861.31 |
| 4,095,457 | 6/1978 | Koda et al. | 73/597 |
| 4,183,244 | 1/1980 | Kohno et al. | 73/861.28 |

Primary Examiner—Charles A. Ruehl
Attorney, Agent, or Firm—Bruce L. Birchard

[57] ABSTRACT

By detecting the instant of a selected zero-crossing of a received ultrasonic signal rather than relying on the instant the amplitude of that received signal exceeds a predetermined reference amplitude in excess of zero, a transit-time measuring instrument can be realized which is free from the measurement errors normally arising from acoustic signal attenuation in the medium through which it passes.

6 Claims, 13 Drawing Figures

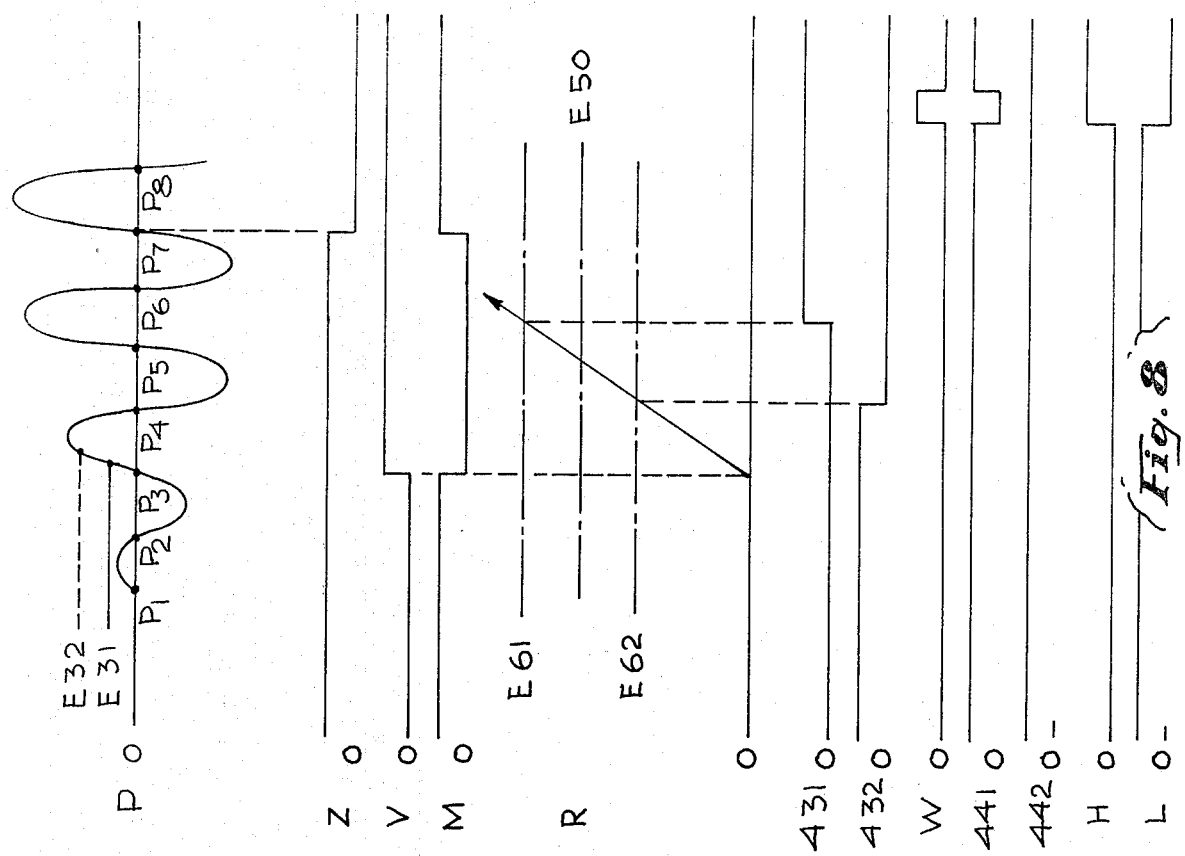
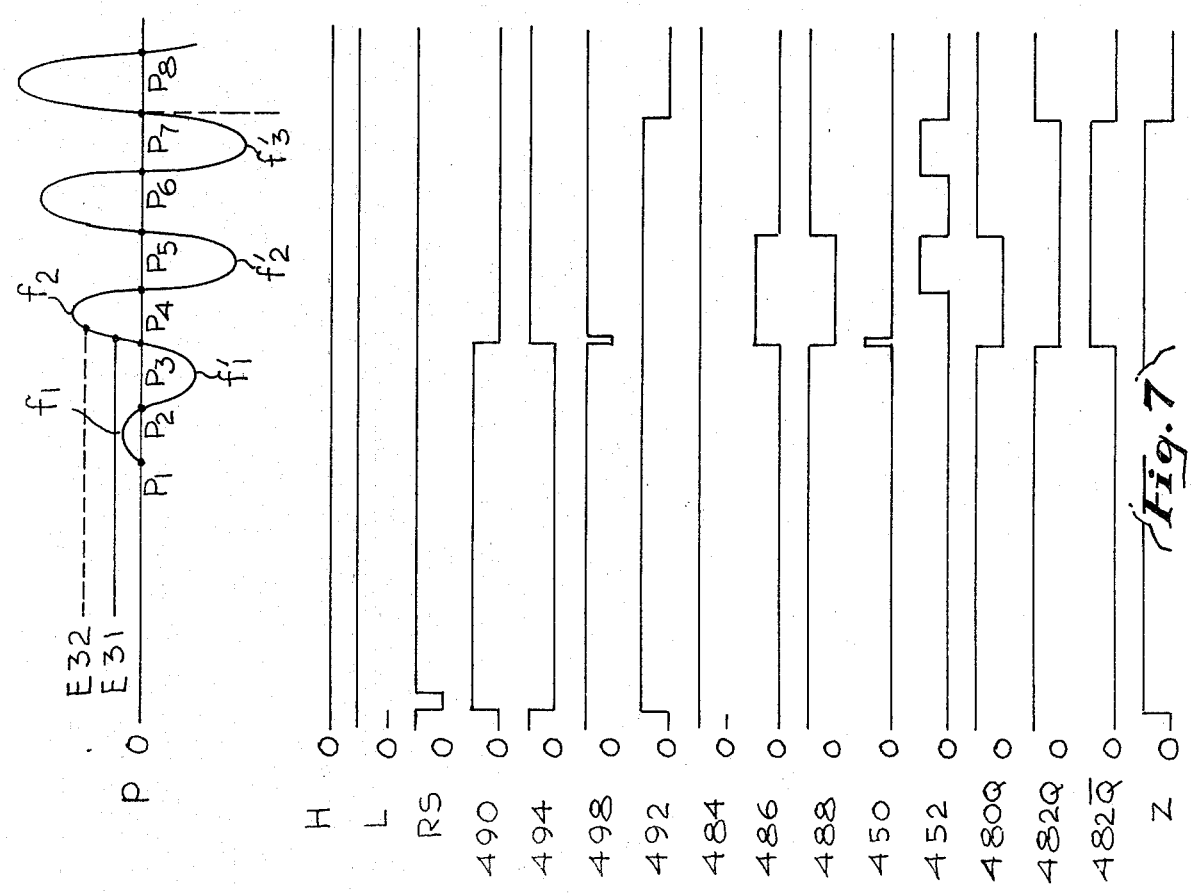

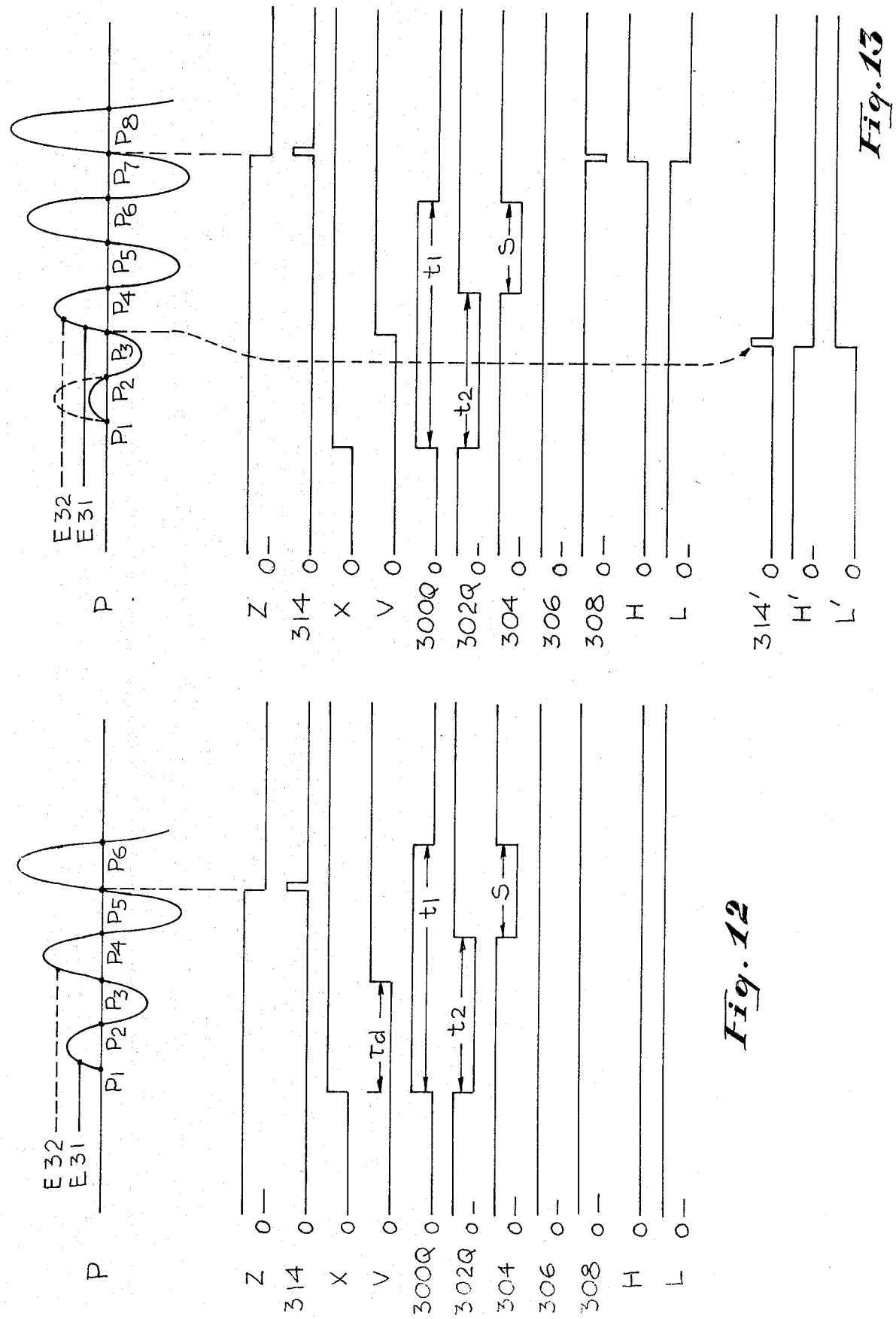

ULTRASONIC MEASURING INSTRUMENT

RELATED COPENDING APPLICATIONS

This application is related to U.S. patent application Ser. No. 928,322 entitled "Ultrasonic Flow Rate Measuring Apparatus," filed July 26, 1978, and to U.S. patent application Ser. No. 35,467 entitled "Ultrasonic Measuring Apparatus" filed May 3, 1979, both applications being assigned to the same assignee as this application. Application Ser. No. 928,322 has issued as U.S. Pat. No. 4,183,244. Application Ser. No. 35,467 is presently pending.

BACKGROUND OF THE INVENTION

1. Field of the Invention

This invention relates to ultrasonic measuring apparatus and, more specifically, to an ultrasonic-signal transit-time measuring instrument wherein the difference between the transit time of the ultrasonic signal and the time for a counter to count a predetermined number of half cycles of the output signal from a voltage-controlled oscillator is detected and such information is used to vary the frequency of the oscillator until such time difference is zero, the transit time for the ultrasonic signal being determinable from such varied oscillator frequency.

2. Prior Art

Ultrasonic-signal transit-time measuring devices have been described in the co-pending applications set forth herein and, in flowmeter systems, are described in an article entitled *Fuji Ultrasonic Flowmeter* appearing at pages 29 to 38 of the journal *Fuji Jiho*, volume 48, No. 2, published by Fuji Electric Company, Ltd. of Tokyo, Japan. In such systems, not utilizing this invention, an ultrasonic acoustic signal emanating from a transmitting transducer is received by an acousto-electric transducer after it passes through the medium being measured.

The electrical signal from this latter transducer is amplified and compared with first and second reference voltages. Comparison with the first voltage produces a "signal arrival" pulse, if the received signal exceeds the first reference voltage. Counting of pulses synchronized with the received signal then occurs for a predetermined number of counts.

If the received signal is attenuated by the medium unduly the received signal will not exceed the first reference voltage and the "arrived" signal will be delayed until a succeeding half-cycle of amplitude greater than the first reference voltage occurs. This delay results in measurement errors which are undesirable.

Therefore, it is an object of the present invention to overcome the general disadvantages of the prior art devices.

It is a further object of this invention to provide a transit-time measurement instrument which gives accurate measurements despite random attenuation, in the measurement medium, of the acoustical signal passing therethrough.

SUMMARY OF THE INVENTION

While the amplitude of an acoustical signal passing through a medium may vary randomly, the period of the signal remains constant. This invention relies on that fact and detects a selected zero-crossing point on the received-and-transduced acoustical wave and treats the instant of zero crossing as the instant of signal arrival at the receiving transducer, rather than relying on the instant at which the received acoustical signal exceeds a predetermined amplitude level.

BRIEF DESCRIPTION OF THE DRAWINGS

The nature of the present invention can best be understood from the description set forth hereinafter taken in conjunction with the accompanying drawings, in which:

FIG. 7 is a timing diagram for certain internal operating functions of the instrument of FIG. 1 under conditions of attenuation of the acoustical signal;

FIG. 8 is a timing diagram for certain operating functions in FIGS. 2 and 3 under the conditions of FIG. 7;

FIG. 12 is a timing diagram for certain internal operating functions of the instrument of FIG. 10; and, FIG. 13 is a timing diagram for certain internal operating functions of the instrument of FIG. 10.

DESCRIPTION OF THE PREFERRED EMBODIMENTS

Figure 1:
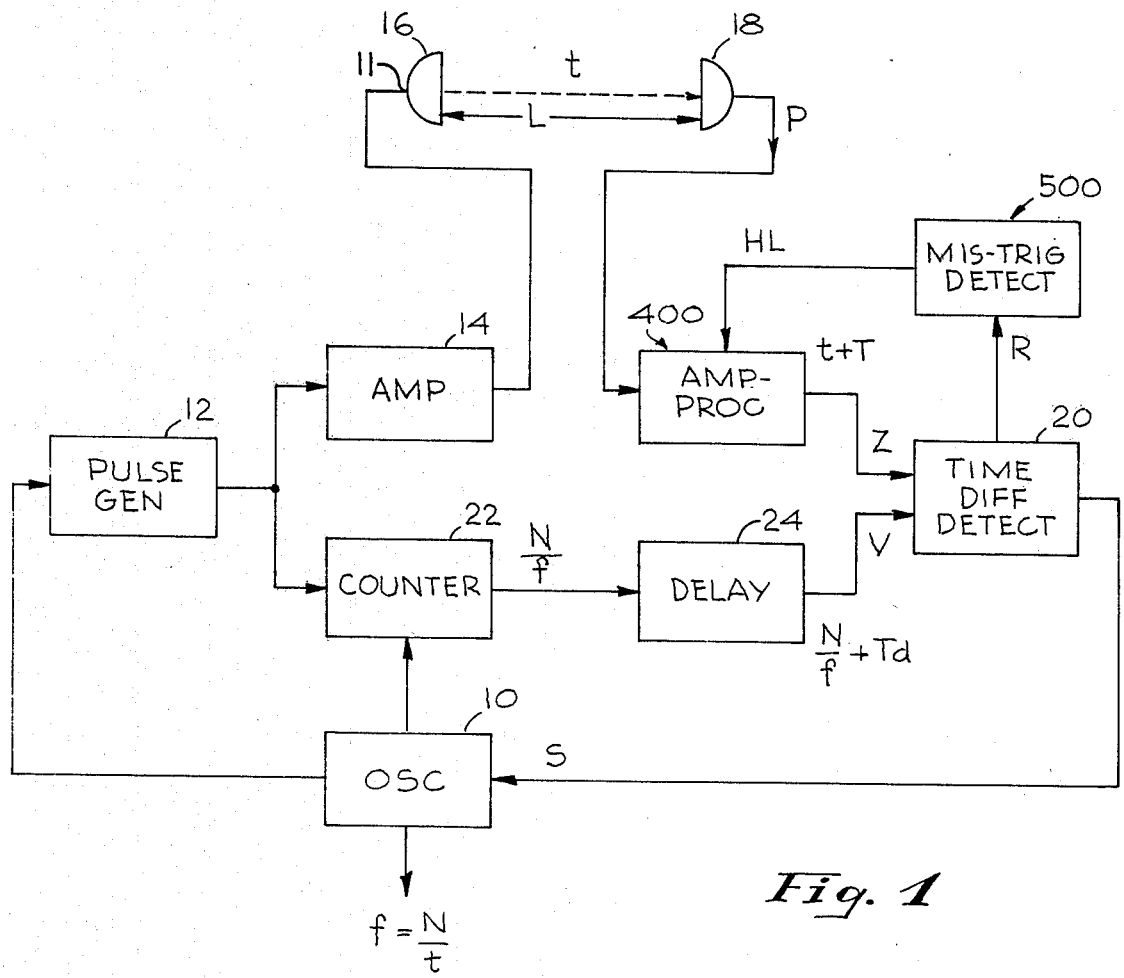
FIG. 1 is a block diagram of an acoustical-signal transit-time measurement instrument according to the present invention.

In FIG. 1, oscillator 10 is of the voltage controlled variety, i.e., output frequency is a function of applied control voltage level. Such oscillators have widespread use. The nominal frequency of oscillator 10 for this application may be in the range from 0.5 MHz to 1.0 MHz.

Signals from oscillator 10 are supplied to synchronous pulse generator 12 which produces output pulses in synchronism with the output signal from oscillator 10.

Such pulses are supplied to amplifier 14 and, thence, in amplified form, to excitation terminal 11 of transmitting transducer 16. Transducer 16 transforms the electrical pulses into acoustical pulses which are transmitted through the medium (not shown) subject to measurement, to receiving transducer 18 which transforms acoustical signals into corresponding electrical signals. Such transducers are readily available and are of piezoelectric materials such as barium titanate or quartz.

Transducers 16 and 18 may be mounted on a wall member (not shown) which may be part of a tubular passage in the event the measurement instrument is to be used in a flowmeter, or on the wall of a container in the event the instrument is to be used as a level gauge. The reference letter "L" in FIG. 1 denotes the transit distance of the acoustical signal in the measurement medium or media and the reference letter "t" denotes the corresponding transit time for the signal.

The output signal P from receiver-transducer 18 is coupled to amplifier-processor 400, the details of which will be described in connection with the description of FIG. 4. Amplifier-processor 400 produces an arrival signal Z which is coupled to time-difference detection circuit 20, the details of which will be set forth in connection with the description of FIG. 2.

Counter 22 counts pulses derived from oscillator 10. It starts counting when it receives a pulse from generator 12 and produces a counting operation "end" signal when its count reaches a predetermined number "N". Such counters are well known in the art and need not be described here.

Delay circuit 24 delays the output "end" signal from counter 22 by a period $T_d$ which approximates the total time for the acoustical signal to propagate through the wall of the container and for the corresponding electrical signals to pass through amplifiers 14 and 400, plus 2 microseconds where the acoustical signal is at 0.5 MHz. Well known analog or digital delay devices may be used.

Figure 2:
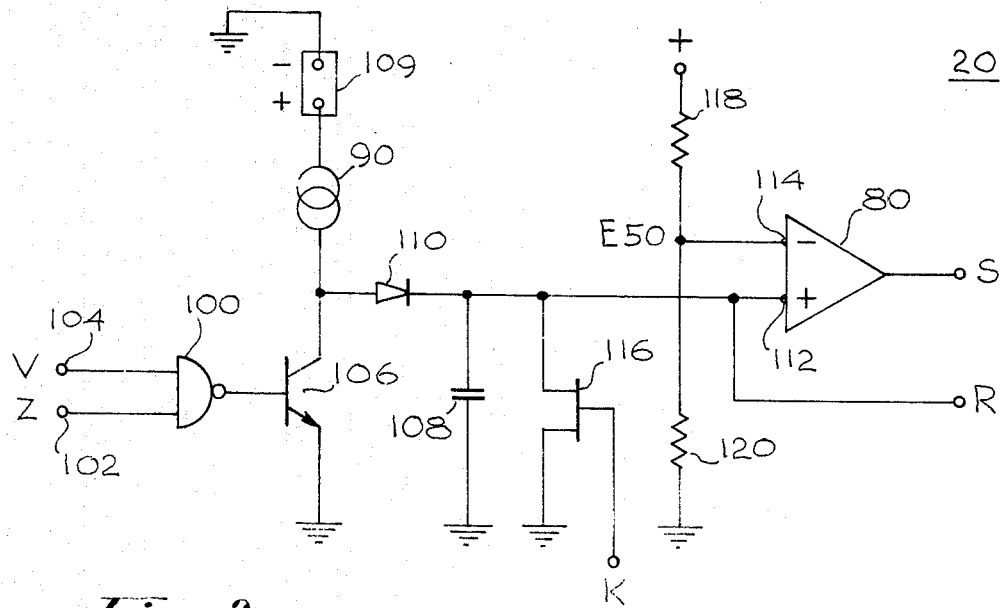
FIG. 2 is a schematic circuit diagram of a first portion of the instrument of FIG. 1.

The details of time-difference detector 20 are shown in FIG. 2. In FIG. 2 NAND-gate 100 has an input terminal 102 coupled to receive the output signal "V" from delay circuit 24. When the arrival signal "Z" applied to input terminal 104 and the delay output signal "V" applied to terminal 102 are simultaneously present the output "ones", the output signal from gate 100 is ended and transistor 106 is cut off. Constant current circuit 90 then begins charging condenser 108 from source 109 through diode 110. Constant current circuit 90 in combination with transistor 106, diode 110 and condenser 108 constitute a RAMP circuit which produces a ramp signal "R". Ramp signal "R" is applied to differential amplifier 80 at terminal 112. Ramp signal "R" continues to build until arrival signal "Z" becomes a "zero" indicating actual signal arrival at transducer 18. At that time transistor 106 begins to conduct stopping ramping action.

To terminal 114 of differential amplifier 80 there is applied a reference voltage E50.

An "on-off" control signal comprising a "1" pulse of length exceeding the time constant of capacitor 108, in combination with transistor 116 when it is conducting, is applied to terminal K after a measurement cycle, from a pulse source not shown, synchronized with pulse generator 12. Similarly, in FIG. 3, a check pulse in the form of a "1" of short duration is applied to terminal "W" from a pulse source, not shown, synchronized with pulse generator 12. The time of such application is at the end of a measurement cycle.

Differential amplifier 80 produces an output signal "S" which is the voltage difference between reference voltage E50 and ramp signal R.

Field effect transistor 116 discharges condenser 108 in response to control signal "K".

Resistors 118 and 120 act as a voltage divider to set the level of voltage E50.

NAND-gate 100 and transistor 106 may be a type SN75451. Diode 110 may be a 1S953.

Field-effect transistor 116 may be a VCR2N.

Differential amplifier 80 may be an LM301A.

The basic circuit of FIG. 1 operates as follows. The control voltage applied to oscillator 10 and, consequently, the frequency of its oscillation are varied, in response to the output signal S, in such a direction as to bring S to zero. The resultant frequency of oscillator 10 is determined at this condition and the transit time t is determined from this frequency. If the oscillation frequency is "f", the time interval required for the counter 22 to count a predetermined number N of the oscillator output cycles is N/f. Since there is a feed-back loop, including time-difference detector circuit 20, to make N/f equal to the transit time of the acoustic signal through the measurement medium, then the equation N/f=t or f=N/t applies. Thus, the frequency f is the reciprocal of the acoustic pulse transit time multiplied by the number of pulses, i.e., f=N/t. The transit time can be determined directly from the frequency, therefore.

In conventional systems the time of arrival of the acoustic signal at receiver transducer 18 is determined as the moment the amplitude of the electrical signal from transducer 18 exceeds a reference voltage. If there is a sudden attenuation within the acoustical signal transmitting medium the first cycle of the received acoustical signal may not be of sufficient amplitude to exceed the reference voltage. Thus, succeeding cycles of the received signal must be awaited before an "arrival" signal will be generated. This missing of the first cycle (or even additional cycles,) of the received signal will cause errors in transit time measurement. The present invention avoids that problem.

Figure 3:
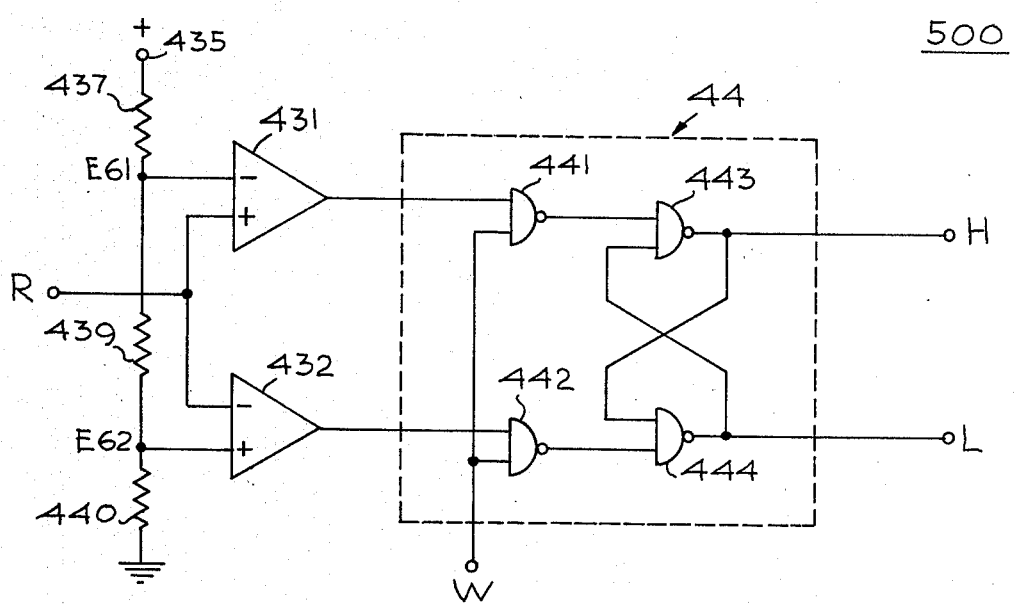
FIG. 3 is a schematic circuit diagram of a second portion of the instrument of FIG. 1.

Mis-trigger detection circuit 500 is one of the circuits which assures the superior performance of the instrument according to this invention. In FIG. 3 the details of that circuit are shown. Mis-trigger detector circuit 500 includes comparators 431 and 432 and a re-settable flip-flop 44 with a clock gate. Comparators 431 and 432 are provided with respective reference voltages E61 and E62 produced from source 435 by means of a voltage divider comprising resistors 437, 439 and 440. Comparators 431 and 432 serve to determine whether the ramp voltage R is within the range between the two reference voltages E61 and E62. As was indicated in connection with FIG. 2, ramp voltage R is proportional to the time difference. The R.S. flip-flop 44 comprises four NAND-gates 441, 442, 443 and 444 and is connected to receive the outputs of the two comparators 431 and 432 and a check pulse "W", and to produce two complementary output signals H and L. As indicated, $\overline{H}=L$ and $\overline{L}=H$. When the duration N/f required for the counter 22 to count the number N of output cycles from oscillator 10 of frequency f is equal to the transit time of the acoustic signal in the measurement medium, then the ramp voltage R of the RAMP circuit becomes equal to the reference voltage E50 of the differential amplifier 80 in FIG. 2. Purely by way of example, in this embodiment the reference voltage E50 can be set at 5 V. Then the reference voltages E61 and E62 are set at:

E61=6 V.

E62=4 V.

The setting of the reference voltages E61 and E62 is dependent upon the magnitude of the period $T_p$ of the acoustic signal and upon the gradient of ramp voltage R (i.e., the charging rate of the RAMP circuit).

The circuit of amplifier-processor 400 differs from that of prior art amplifiers in transit time measuring instruments. In FIG. 4, amplifier-processor 400 includes comparators 450 and 452 adapted to receive at their input terminals 454 and 456, respectively, output signal P of transducer 18. The ultimate action of amplifier-processor 400 is to produce the arrival signal Z at its output terminal 458.

Comparator 450 receives at its remaining input terminal 460 reference voltages E31 or E32, and serves to produce an output "1" signal when the magnitude of the signal P exceeds the reference voltage E31 or E32. Reference voltages E31, E32 are produced by a voltage divider comprising resistors 462, 464, 466 and a power supply, not shown connected between terminal 468 and ground. E31 is less than E32.

When the output signal L of mis-trigger detector 500 is a "1", transistor 470 is in an "on" state, so that comparator 450 receives the reference voltage E31. When the signal L is a "zero", the transistor 470 is in an "off" state and comparator 450 has voltage E32 applied to its terminal 460. Whether E31 or E32 should be applied to terminal 460 depends on the level of attenuation, as will be described hereinafter. The comparator 450 is provided with a strobe terminal 472 to permit holding its output signal at "zero".

In this embodiment, this holding of the output state takes place after the comparator 450 produces its output signal representing that the magnitude of the signal P has first exceeded the reference voltage E31 or E32. Similarly, the other comparator 452 is connected to receive the output signal P at its input terminal 456 and to receive at its other input terminal 474 a reference voltage of zero volts. In this embodiment the comparator 452 produces a "1" output signal when the magnitude of the signal P crosses the zero volt level in the negative-going direction. Comparator 452 is also provided with a strobe terminal 476 to hold the state of the output of this comparator, in response to the output signal from a counter comprising J-K flip-flops 480 and 482, each of which is connected to receive the output signal of comparator 452 at its T-input terminal. The control circuit comprises three NAND-gates, 484, 486 and 488. Gate 484 is connected to receive the output signal H of the mis-trigger detector 500 and the Q-output of flip-flop 482. Gate 486 is connected to receive the output signal L of the mis-trigger detector 500 and the Q-output of flip-flop 480. Gate 488 is connected to receive both the outputs of gates 484 and 486. The output of gate 488 is connected to the J-input terminal of the flip-flop 482, the $\overline{Q}$-output of which, in turn, is connected to the J-input terminal of flip-flop 480 and to the strobe terminal 476 of comparator 452.

The amplifier 400 is further provided with a logic circuit comprising NAND-gates 490 and 492. The NAND-gates 490 and 494 constitute an R-S flip-flop. The NAND-gate 490 is connected to receive a reset input signal RS from terminal 496 and its output is led to the NAND-gate 494, the NAND-gate 498 and a strobe terminal 472 of the comparator 450. A set input terminal of the NAND-gate 494 is connected further to receive a Q-output of the flip-flop 482. The output of the NAND-gate 494 and the Q-output of the flip-flop 482 are led to the NAND-gate 442, which produces as its output the arrival signal Z representing an arrival of an acoustic signal at the transducer 18. The NAND-gate 498 is connected to receive not only the output of the NAND-gate 490 but also the output signal of the comparator 450.

Purely by way of example comparators 450, 452, may be semiconductor type MC1414. Flip-flops 480, 482 may be type SN74107. Transistor 470 may be a 2SC943.

NAND-gates 484, 486, 488, 490, 492, 494 and 498 may be type SN7400.

In FIG. 3, comparators 431 and 432 may be type LM339A. NAND-gates 441 and 444 may be type SN7400.

Operation of the foregoing circuit may best be understood by referring to FIGS. 5 through 9.

Figure 4:
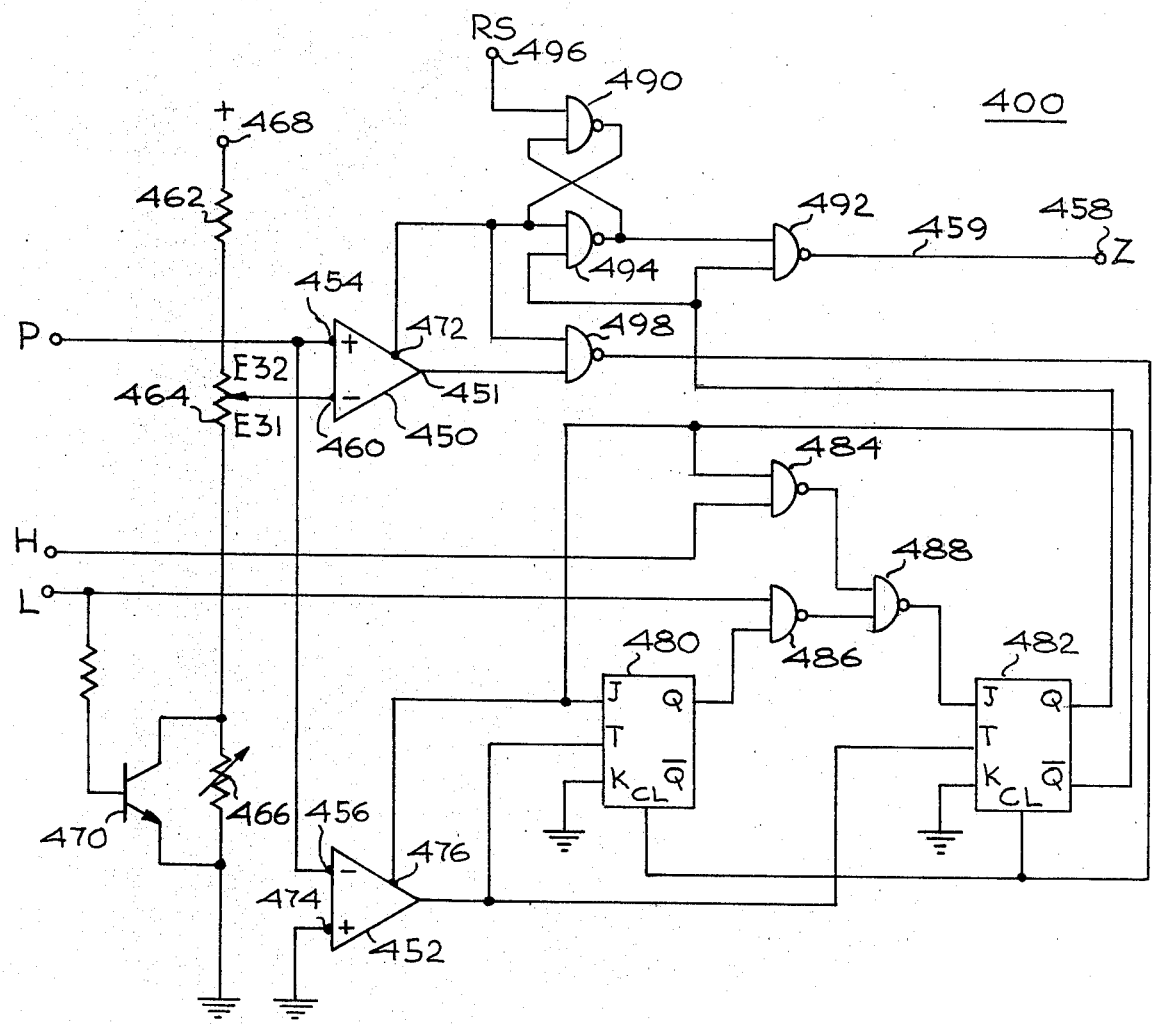
FIG. 4 is a schematic circuit diagram of a third portion of the instrument of FIG. 1.
Figure 6:
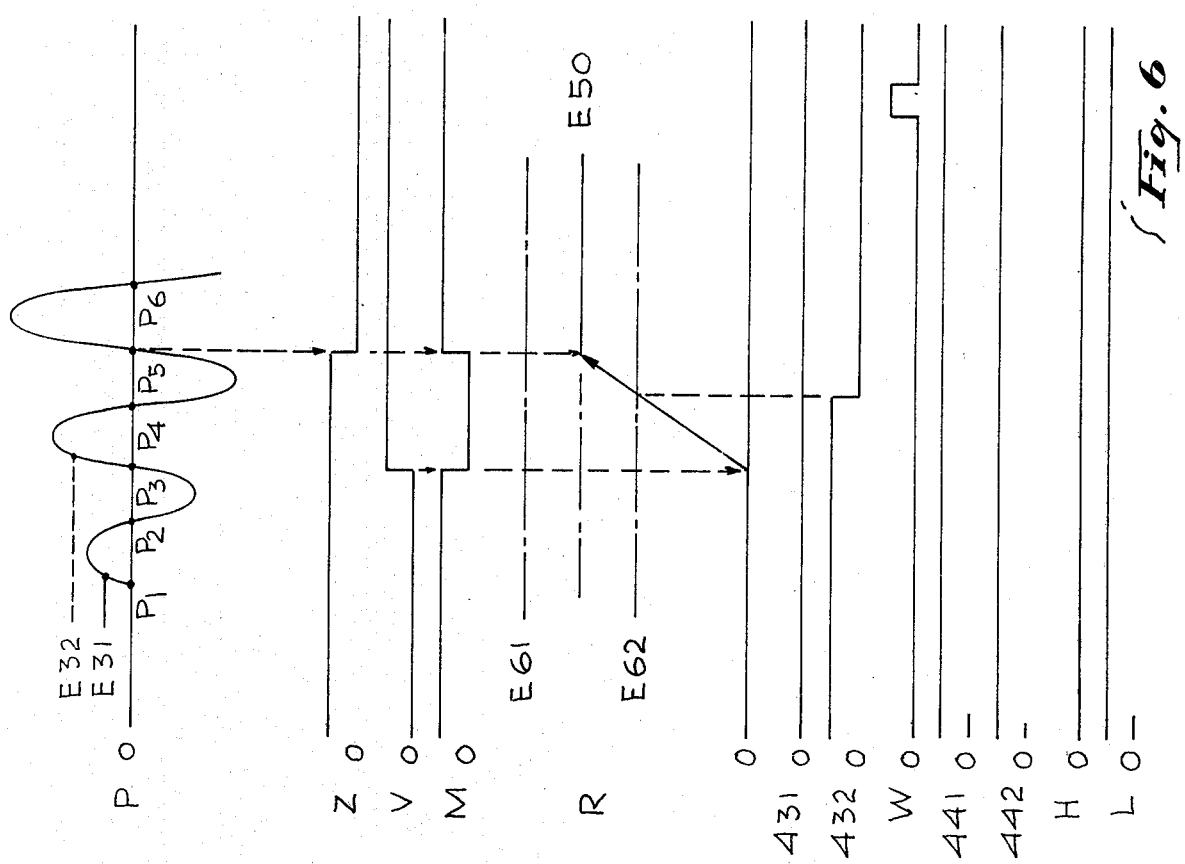
FIG. 6 is a timing diagram for certain operating functions in the circuits of FIGS. 2 and 3 under the conditions of FIG. 5.
Figure 5:
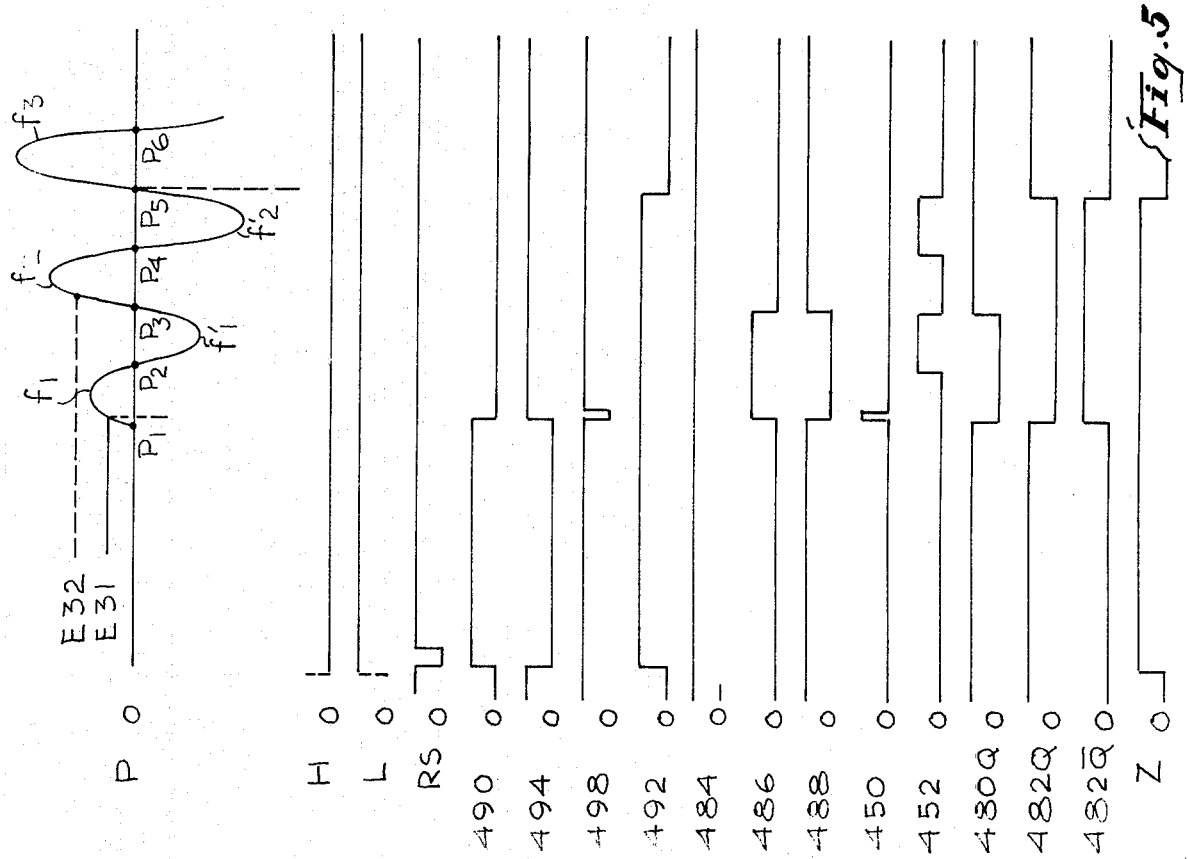
FIG. 5 is a timing diagram for certain internal operating functions of the instrument of FIG. 1 under conditions of no untoward acoustical signal attenuation.

FIG. 5 shows time-varying output signals at various points in FIG. 4, in the case where the acoustic signal is free of attenuation. FIG. 6 shows output signals at various points in FIG. 2 and FIG. 3, in the same case. At first, suppose that the comparator 450 in FIG. 4 is supplied with the voltage $E_{31}$ as its reference voltage, and that the output signal L of the mistrigger detector 500 is a "1". Before starting the measurement, a reset signal RS is supplied to the NAND-gate 490, in the form of a "0" signal, as shown in FIG. 5 line RS. By receiving this reset signal RS, the NAND-gate 490 turns its output to a "1" signal. Consequently, the comparator 450 is released from control of the strobe connection, and goes into a stand-by condition. In this state, as the output signal of the NAND-gate 490 is a "1", either of two inputs of the NAND-gate 492 is a "0", and therefore the output signal of the NAND-gate 492, i.e. the arrival signal bus 459 comes to a "1" state (this does not mean that the acoustic signal has arrived, but an arrival signal bus level of "0" means that it has arrived). After that, when the acoustic signal reaches the transducer 18 and output signal P appears at input terminal 454 of the comparator 450, if the magnitude of the first wave $f_1$ of the signal P exceeds the reference voltage $E_{31}$, then a "1" signal will appear at the output terminal 451 of the comparator 450.

Consequently, the output signal of the NAND-gate 498 becomes a "0", and by this, both the flip-flops 480 and 482 are cleared, so that both their Q-outputs come to "0" signals and the $\overline{Q}$-output of the flip-flop 482 comes to a "1" signal. This $\overline{Q}$-output signal of "1" serves to release the comparator 452 from the holding of its output to a stand-by condition. And the Q-output signal of the flip-flop 482, a "0", causes the output signal of the NAND-gate 494 to return to "1". By this, the output signal of the NAND-gate 490 returns to "0", so that the comparator 450 is subject to holding of its output, again. Thus, the output signal of the comparator 450 appears as a pulse of a very narrow width, when the signal P exceeds the reference voltage $E_{31}$. On the other hand, a Q-output signal of the flip-flop 480 of "0" causes the NAND-gate 486 to turn its output to a "1" signal, and by this, the NAND-gate 488 shifts its output to a "0" signal. After that, flip-flop 480 turns its Q-output to a "1" signal, and NAND-gate 488 turns its output to a "1" signal. Subsequently, by a second negative wave $f_2$ of the signal P, a second output pulse of the comparator 452 is produced, and when this pulse is ended, the flip-flop 482 returns its Q-output to a "1" signal. As a result, the NAND gate 492 turns its output to a "0" signal. That is, the arrival signal Z, a "0", is sent out, to represent that the acoustic signal has reached the transducer 18 at the time instant $P_5$, the fifth zero-crossing of the signal P.

At the instant $P_5$, when the "zero" representing arrival signal Z is sent out, the charging operation in the RAMP circuit is ended, and the ramp voltage R stops ramping and remains a steady voltage. The value of this voltage R in this state is within a range between the reference voltages $E_{61}$ and $E_{62}$. Under this condition, therefore, if the check pulse W is applied to the R-S flip-flop 44 with the clock gate (FIG. 3), no variation appears in the output signal of the flip-flop 44, i.e. in the output signal H or L of the mistrigger detector 500. Thus, using the check pulse W, it can be found that the correct detection of the acoustic signal arrival has taken place, so that the voltage $E_{31}$ may continue to be supplied as the reference voltage to the comparator 450 in the measurement processes which follow.

FIG. 6 shows time-varying output signals at various points in FIG. 4, if the acoustic signal is subjected to attenuation. FIG. 7 shows output signals at various points in FIG. 2 and FIG. 3, in the same case. When attenuation of the acoustic signal occurs in the situation where the comparator 450 is supplied the voltage $E_{31}$ as its reference voltage, the amplifier processor 400 and the mistrigger detector 500 perform as follows. At first, a reset signal RS is supplied and the comparator 450 is released from the holding of its output. Due to attenuation, the magnitude of the first wave $f_1$ of the output signal P of the transducer 18 does not reach the reference voltage $E_{31}$, but its second wave $f_2$ has a magnitude exceeding the reference voltage $E_{31}$. At the time $f_2$ exceeds $E_{31}$, the comparator 450 produces its output signal. Then, the performance is as discussed in connection with FIG. 7. The generation of output pulses from the comparator 452 is, however, caused by the second and third negative waves $f_2$ and $f_3$ of the signal P.

The arrival signal Z (a "0") is produced at the time $P_7$ (the end of the third negative wave $f_3$). An apparent transit time of the acoustic signal in the case of FIG. 7 is longer than that in the case of FIG. 5 by time intervals $P_5-P_6$ and $P_6-P_7$, i.e. by a duration of 2T, in spite of an identical actual transit time. This time interval of 2T could cause a measurement error. In this invention, however, in such a case the charging operation in the RAMP circuit is carried out for an extended period only by that duration of 2T; that is, the ramp voltage R gets an extra rise just for that duration 2T, as shown in FIG. 8, so as to exceed the reference voltage $E_{61}$ of the mis-trigger detector 500. Consequently, if a check pulse W is supplied to the mis-trigger detector 500 in this condition, a change of its output signals H and L into their respective negations takes place: the signal L changes from "1" to "0". Therefore, by virtue of operation of the transistor 470, the reference voltage to the comparator 450 is changed to the voltage $E_{32}$. Thus, any tendency to generate the arrival signal Z at an incorrect time, as a result of an acoustic signal attenuation, results in a correction of itself in succeeding measurements.

Figure 9:
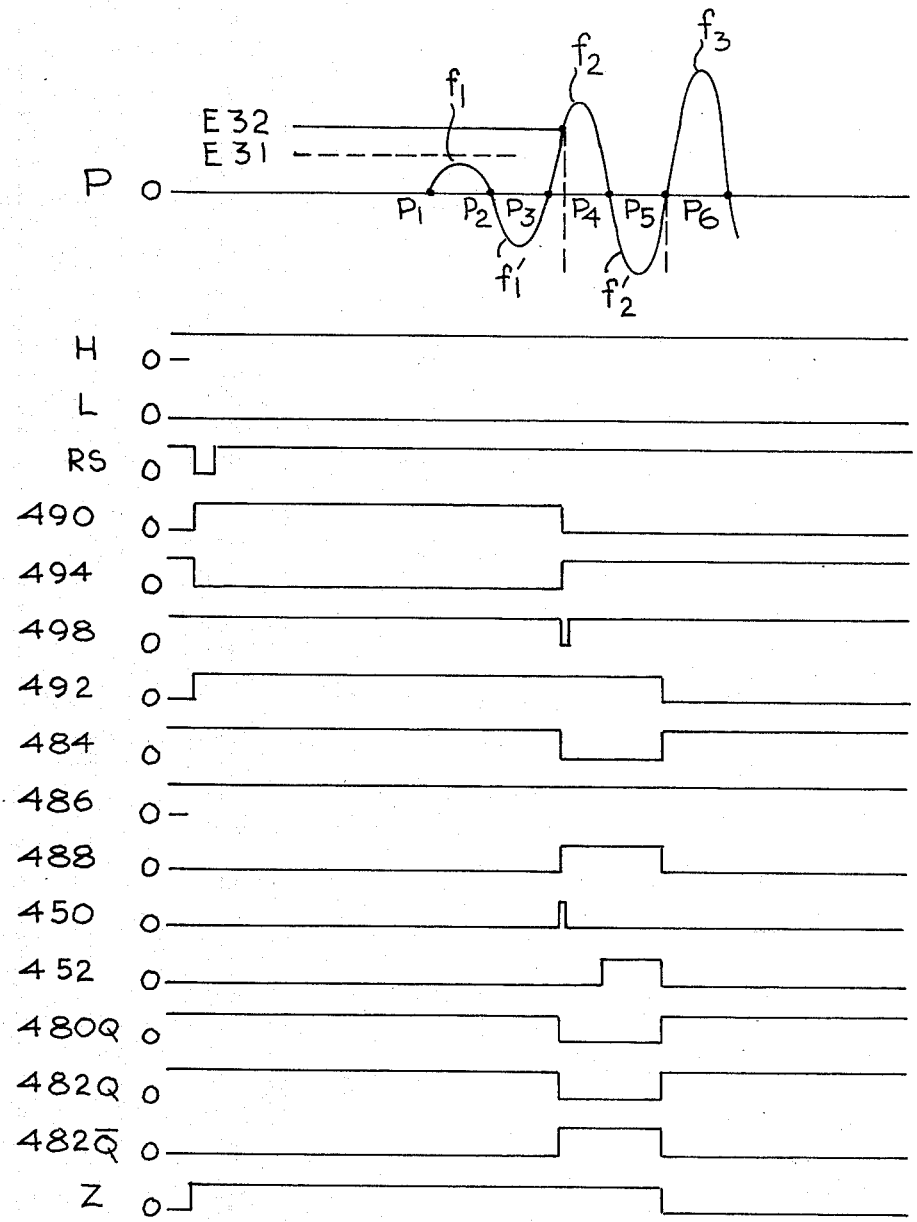
FIG. 9 is a timing diagram for certain operating functions within the instrument of FIG. 1 under continuing acoustical-signal-attenuation conditions.

Suppose that the condition of acoustic signal attenuation continues, and that the comparator 450 continues to be supplied with the reference voltage $E_{32}$. Then, the operation of the amplifier processor 500 is as shown in FIG. 9. When a reset signal RS is supplied, the comparator 450 is released from the holding of its output. After that, when the magnitude of the signal P at its second wave $f_2$ exceeds the reference voltage $E_{32}$, the comparator 450 produces its output signal. Consequently, the process just described takes place, as shown in FIG. 9. However, the generation of an output pulse of the comparator 452, caused by the second negative wave $f'_{2'}$ causes the flip-flop 482 to produce its Q-output signal with the result that the arrival signal Z (a "0") is produced at the time of $P_3$. Then, again a time interval of 2T comprising intervals $P_3-P_4$ and $P_4-P_5$ can cause a measurement error. In such a case, however, the ramp voltage R in the RAMP circuit stops rising, before reaching the reference voltage $E_{62}$ of the mis-trigger detector 500. Supplying a check pulse W can then cause the signal L to turn from a "0" to a "1", so that the operation as shown in FIG. 5 takes place and correct results are realized.

As was previously stated, in the present invention, the acoustic signal arrival at the receiving transducer can be determined as the instant when a predetermined number of zero-crossings of the transducer output signal P have appeared, for example at the instant $P_5$ of its fifth zero-crossing. As a result, the correct detection of the acoustic signal arrival can be attained consistently. And in one of its embodiments, not shown, the invention can be further provided with means to prevent the output signal S of the differential amplifier 80 (FIG. 2) from reaching the oscillator 10 on the occurrence of the operation shown in FIG. 7. By this means, the frequency of the oscillator 10 can be held at its value given in the preceding measurement. Such holding of the oscillator frequency (i.e. the measurement result) can prevent a measurement error caused by the signal S's carrying faulty time-difference information in the example of FIG. 7, though this is an error of a very short duration.

In case of applying this invention to an acoustic flowmeter, the system would include two oscillators and a switchover circuit, such switchover circuit being connected between the transducers 16 and 18 and the transmitting and receiving amplifiers 14 and 400. The transducers 16 and 18 are mounted on a tube wall of the measurement passage obliquely opposed to each other, as shown in the Japanese laid-open specification No. 130261 of 1974. A transit time $t_1$ of the acoustic signal with flow of the measured fluid (e.g. in case of the signal transit from the transducer 16 to the transducer 18) is transformed into a frequency $f_1$ of one of the oscillators; and another transit time $t_2$ against flow (e.g. in case of the signal transit from the transducer 18 to the transducer 16, measured after changing over a connection in the switch-over circuit) is transformed into a frequency $f_2$ of the other oscillator. Then, a difference between the oscillation frequencies $f_1$ and $f_2$ gives the flowrate of the measured fluid.

The reset signal RS in above embodiments of the invention can be produced by some means either synchronously with the output signal of the synchronous pulse generator 12 or just before an expected generation of the output signal P at the transducer 18. The latter case is preferable to eliminate noises prior to the generation of the output signal P. And as to the check pulse W, it is preferable to produce this at the time near to the end of one measurement period.

Figure 10:
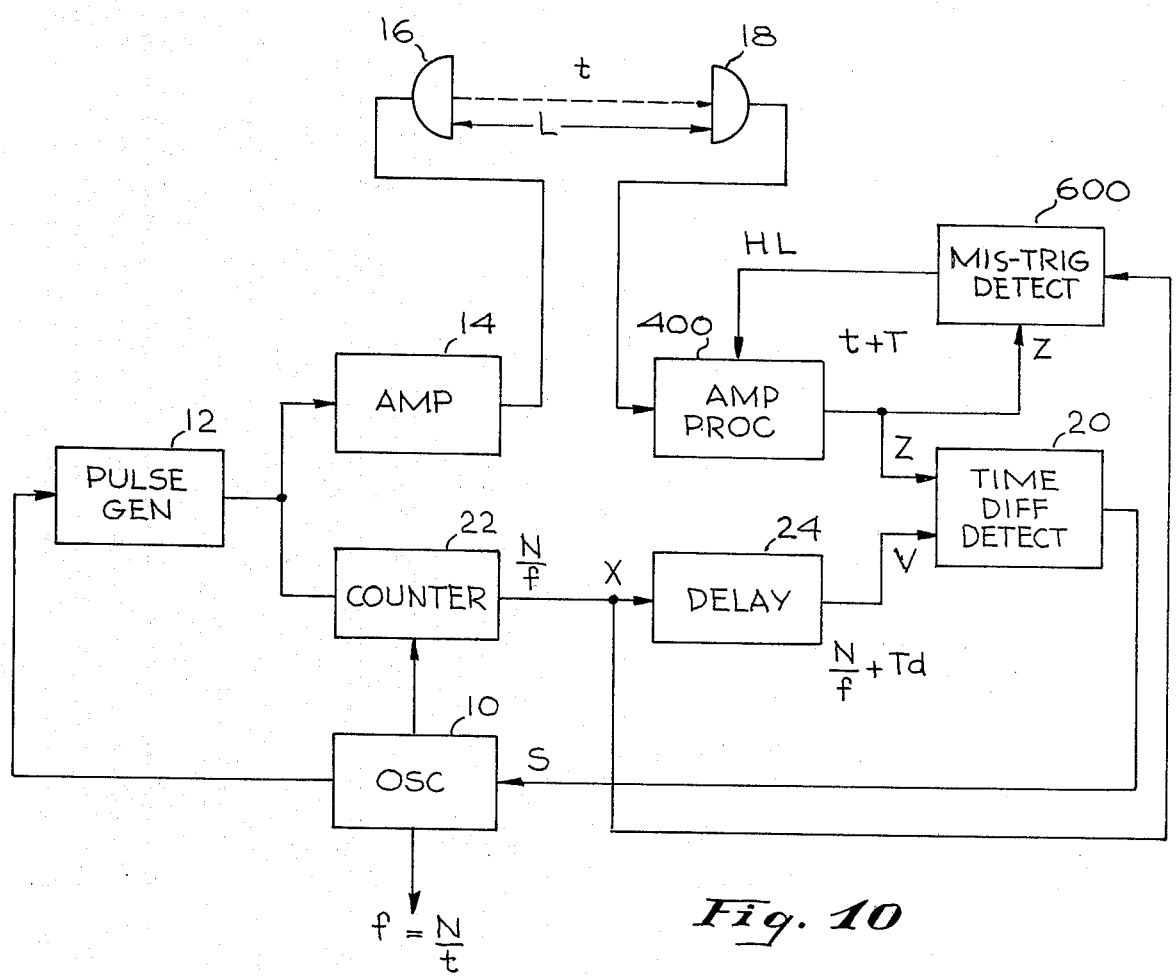
FIG. 10 is a block diagram of an alternative form of the invention of FIG. 1.

FIG. 10 is a block diagram showing another embodiment of the invention. Like characters of reference are used to designate like parts as shown in FIG. 1. The main difference between this embodiment and that of FIG. 1 is in the mis-trigger detector which indicates whether the acoustic signal propagation is normal or abnormal. The mistrigger detector 600 used in this embodiment is shown in more detail in FIG. 11. It comprises two monostable multivibrators 300 and 302, a NAND-gate 304, and an R-S flip-flop with a clock gate. The R-S flip-flop comprises four NAND-gates 306, 308, 310 and 312. This mis-trigger detector 600 is connected to receive the output signal X of the counter 22 and the output signal Z of the receiving amplifier 400, as shown in FIG. 10. The pulse width $t_1$ of an output pulse of the monostable multivibrator 300 is set at a duration ($T_d+S_1$) longer than the delay time $T_d$ of the delay circuit 24 by a time interval $S_1$. The pulse width $t_2$ of an output pulse of the other monostable multivibrator 302 is set at a duration ($T_d+S_2$) longer than the delay time $T_d$ by a time interval $S_2$. And in this embodiment they are set as $S_1=3T$ and $S_2=T$, so that $S=S_1-S_2=2T$, where T is a half cycle period of the acoustic signal. When the oscillating frequency of the acoustic signal is 1 MHz, then $T=1\mu S$, and when it is 0.5 MHz, then $T=2\mu S$. The monostable multivibrator 300 sends out its Q-output, while the other monostable multivibrator 302 sends out its $\overline{Q}$-output. The NAND-gate 304 is adapted for NAND responses to these Q and $\overline{Q}$-output signals. The mis-trigger detector 600 serves to produce a "0" pulse signal of pulse width S at a predetermined time interval $t_2$ after the generation of the output signal X from the counter 22, so as to indicate that the acoustic signal is propagating normally if the output signal Z (a "0") is produced during the term of pulse signal S. Reference numeral 314 denotes a monostable multivibrator responsive to the output "zero" signal of Z, to produce at its output a pulse of very short width.

The operation of the mis-trigger detector 600 is as follows.

Under conditions of normal propagation of the acoustic signal various signal relationships are shown in FIG. 12. When an output signal is produced from the synchronous pulse generator 12, then the counter 22 starts counting the output half-cycles of the oscillator 10 operating at frequency f, and the transducer 16 sends out an acoustic pulse signal. At a time interval N/f after that, the counter 22 produces its output signal X (i.e. the counting operation end signal), in response to which the monostable multivibrator 300 sends out its Q-output signal with a pulse width $t_1$ and the other monostable multivibrator 302 sends out its $\overline{Q}$-output signal with another pulse width $t_2$. Consequently, the NAND-gate 304 produces an output pulse signal (a "0") with a pulse width S. Under such a situation, an output signal Z of the receiving amplifier 400 (i.e. an output pulse of the monostable multivibrator 314), if produced, does not cause the output signals of the NAND-gates 306 and 308 to vary, and therefore no change appears in output signals H and L of the mis-trigger detector 600. And no change occurs in an ON-OFF control signal to the transistor 470 of FIG. 4.

In the case of abnormal (i.e. attenuated) propagation of the acoustic signal the various signals are as shown in FIG. 13. This chart represents a case similar to that shown in FIG. 8 and the mistrigger detection in that case. When the receiving amplifier 400 produces its output signal Z (a "0") at the time $P_7$ (similarly shown in FIG. 8), the NAND-gate 308 changes its output signal, since at that time the NAND-gate 304 does not have a "0" output state. Consequently, the output signal L of the mis-trigger detector 600 changes to "0", so that the reference voltage to the comparator 10 changes to the voltage $E_{32}$ for succeeding measurements.

If an acoustic pulse signal with its first cycle of a large magnitude as shown by a dotted line in FIG. 13 and the comparator supplied with the reference voltage $E_{32}$, so that the magnitude of the first wave exceeds the reference voltage, then the output signal Z of the receiving amplifier 400 can appear at a time instant $P_3$. In such a case, in response to the output signal Z (a "0") of the receiving amplifier 400, the monostable multivibrator 314 produces a "1" output pulse, as shown in FIG. 13 line 314 so that every input to the NAND-gate 306 becomes a "1", which turns its output signal to "0". Consequently, the output signal of the NAND-gate 310, i.e. the output signal L of the mis-trigger detector 600, turns to "1", as shown in FIG. 13 lines H' and L'. Therefore, the reference voltage to the comparator 450 is changed to the voltage $E_{31}$, in succeeding measurements.

The use of this mis-trigger detector 600 is preferable, because it dispenses with initiation of the check pulse W.

Figure 11:
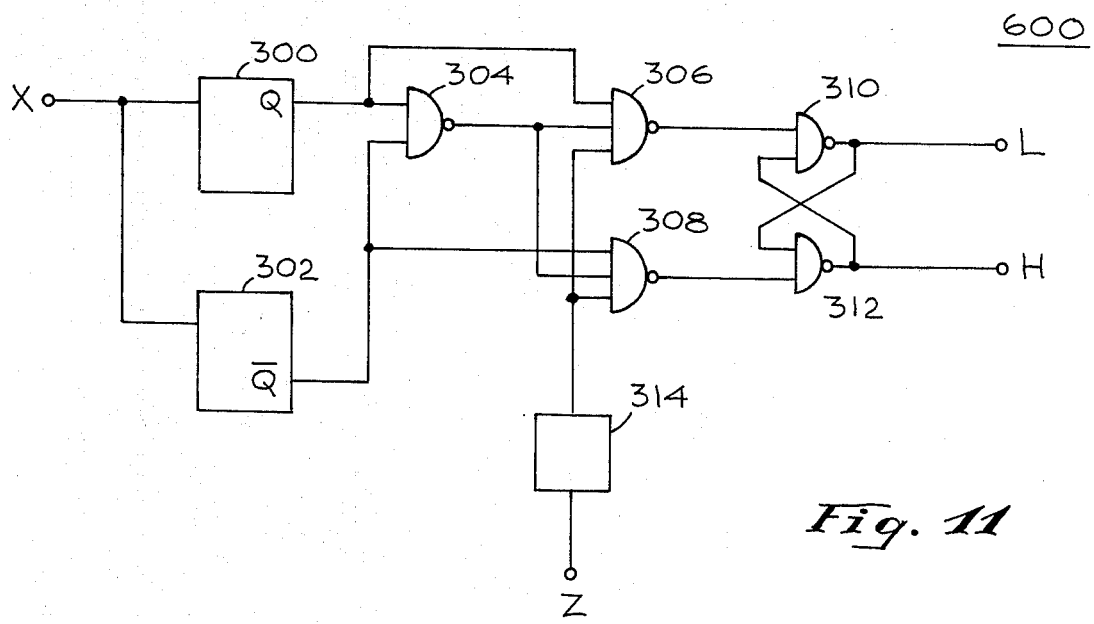
FIG. 11 is a schematic circuit diagram of a portion of the instrument of FIG. 10.

In FIG. 11, the following semiconductor type numbers apply, purely by way of example:

MONOSTABLE CIRCUITS
   300, 302 and 314—SN74122
NAND-GATES
   304, 310, 312—SN7400
   306, 308—SN7410

While particular embodiments of this invention have been shown and described it is apparent to those skilled in the art that modifications may be made without departing from the true scope and spirit of this invention. It is the intention of the appended claims to cover all such modifications.

What is claimed is:

1. An ultrasonic-signal transit-time measuring instrument, including:
   a voltage-controlled oscillator having an output terminal and a control terminal;
   a synchronized pulse generator having a signal input terminal coupled to said output terminal of said oscillator and having a pulse output terminal;
   a transmitting transducer adapted for acoustic coupling to a medium to be tested, said transmitting transducer having an excitation terminal;
   said excitation terminal being coupled to said pulse output terminal for generating an acoustical pulse from said transmitting transducer in response to an electrical pulse applied to said excitation terminal;
   a receiving transducer having an electrical signal output terminal and being responsive to said acoustical pulse, upon its travel through said medium to produce a cyclical electrical signal at said electrical signal output terminal, said receiving transducer being adapted for acoustical coupling to said medium to be tested;
   an amplifier-processor having a first input terminal coupled to said electrical signal output terminal of said receiving transducer, second and third input terminals and a signal-arrival-signal output terminal;
   a counter having first and second input terminals and an output terminal, said first input terminal being connected to said pulse output terminal of said pulse generator, said second input terminal being coupled to said output terminal of said oscillator for the application of an oscillation signal to said second input terminal of said counter;
   means coupled between said second input terminal of said counter and said output terminal thereof for producing, in response to the application of a pulse to said first input terminal from said pulse generator an end-of-count signal corresponding to the end of counting of a pre-determined number of cycles of said oscillation signal applied to said input terminal of said counter;
   a time-difference detector coupled to said output terminal of said counter to receive said end-of-count signal therefrom, said time-difference detector being also coupled to said signal-arrival-signal output terminal of said amplifier-processor to receive a signal-arrival-signal therefrom, said time-difference detector having a correction-signal output terminal and being responsive to said end-of-count signal and said signal-arrival-signal to produce, at its correction-signal output terminal a correction signal corresponding to the time difference between the application of said end-of-count signal and said signal-arrival-signal to said time-difference detector, said correction-signal output terminal of said time-difference detector being coupled to said control terminal of said oscillator, the sign of said correction signal being such as to, when applied to said oscillator, reduce said correction signal;

said amplifier-processor including first and second comparators, each having a signal input terminal, a comparison voltage terminal, an output terminal and a strobe terminal, each of said signal input terminals being coupled to said electrical signal output terminal of said receiving transducer;

said comparison voltage terminal of said first comparator being connected to a source of a first reference voltage greater than zero;

said comparison voltage terminal of said comparator being connected to zero potential;

said output terminal of said first comparator exhibiting a "one" condition when said output signal from said receiving transducer exceeds said first reference voltage;

said output terminal of said second comparator exhibiting a "one" condition when said output signal from said receiving transducer is negative;

second counting means coupled to said output terminal of said second comparator and responsive to signals therefrom to produce an output signal following the occurrence of a predetermined number of output signals from said second comparator;

and NAND-gate means responsive to said output signal from said second counting means for producing a signal representing the arrival time of said acoustical signal at said receiving transducer.

2. Apparatus according to claim 1 which includes, in addition, delay means coupled between said counter and said time-difference detector for eliminating transit time other than in the medium to be measured.

3. Apparatus according to claim 2 in which said delay means are variable in the amount of time delay.

4. Apparatus according to claim 1 in which said time-difference detector includes a ramp-signal output terminal and which apparatus includes a mis-trigger detector having an input terminal connected to said ramp signal output terminal and a pair of output terminals coupled to said amplifier-processor for automatically controlling the magnitude of said first reference voltage in response to the amplitude of said cyclical electrical signal from said receiving transducer.

5. Apparatus according to claim 1 which includes, in addition, mis-trigger means coupled between said output terminal of said counter and said second and third input terminals of said amplifier processor and responsive to said end-of-count signal and said signal-arrival-signal to automatically control the magnitude of said first reference voltage.

6. Apparatus according to claim 5 in which said mis-trigger means includes first and second monostable multivibrators respectively coupled to said counter, each such multivibrator having Q and $\overline{Q}$ output terminals;

a first NAND gate having a first input terminal coupled to said Q output terminal of said first multivibrator and a second input terminal coupled to said $\overline{Q}$ terminal of said second multivibrator, and having an output terminal;

an R-S flip-flop coupled to said output terminal of said first NAND gate, having an output state and having a clock gate input terminal to which a pulse corresponding to said signal-arrival-signal may be applied;

said first monostable multivibrator having an output pulse of width equal to the delay time of said delay means plus the period of three half cycles of said cyclical electrical signal;

said second monostable vibrator having an output pulse of width equal to the time delay of said delay means plus the period of one half cycle of said cyclical electrical signal, said first NAND gate being responsive to said signals from said monostable multivibrators to produce an output pulse of width equal to twice the period of a half-cycle of said cyclical signal;

said R-S flip-flop being responsive to a non-time-overlap of said output pulse of said NAND gate and said signal-arrival-signal to produce a change in its output state.

* * * * *